(12) United States Patent
Coyle et al.

(10) Patent No.: US 8,465,927 B2
(45) Date of Patent: Jun. 18, 2013

(54) **DETECTION OF *NEISSERIA MENINGITIDIS* BY LOOP MEDIATED ISOTHERMAL AMPLIFICATION**

(75) Inventors: Peter Coyle, Belfast Antrim (GB); Derek Fairley, Dundonald Down (GB); James McKenna, Belfast Antrim (GB)

(73) Assignee: Belfast Health and Social Care Trust, Belfast Down (GB)

( * ) Notice: Subject to any disclaimer, the term of this patent is extended or adjusted under 35 U.S.C. 154(b) by 266 days.

(21) Appl. No.: 12/743,115

(22) PCT Filed: Nov. 14, 2008

(86) PCT No.: PCT/GB2008/051061
§ 371 (c)(1),
(2), (4) Date: May 14, 2010

(87) PCT Pub. No.: WO2009/063243
PCT Pub. Date: May 22, 2009

(65) Prior Publication Data
US 2010/0304385 A1  Dec. 2, 2010

Related U.S. Application Data

(60) Provisional application No. 61/002,987, filed on Nov. 14, 2007.

(51) Int. Cl.
*C12Q 1/68* (2006.01)
*C12P 19/34* (2006.01)

(52) U.S. Cl.
USPC .......................... 435/6.12; 435/91.2

(58) Field of Classification Search
USPC ................................. 435/6.12, 91.2
See application file for complete search history.

(56) References Cited

U.S. PATENT DOCUMENTS
2009/0130656 A1 * 5/2009 Whiley et al. ............... 435/6

OTHER PUBLICATIONS

Rychlik et al., Nucleic Acids Research 17(21), 8543-8551 (1989).*
Taha et al., Journal of Clinical Microbiology 43(1), 144-149 (2005).*
Yoshikawa et al., Journal of Clinical Microbiology 42(3), 1348-1352 (2004).*

* cited by examiner

*Primary Examiner* — Kenneth Horlick
(74) *Attorney, Agent, or Firm* — Scully, Scott, Murphy & Presser, P.C.

(57) ABSTRACT

The invention provides a LAMP assay for detection of meningococcal disease, the test comprising at least one nucleic acid primer set capable of detecting *Neisseria meningitides* in a LAMP based molecular test, the primer set being chosen from the primer sets listed in Table 1 as LAMP SETS 1 to 12 comprising SEQUENCE IDs from ID:1 to ID:69. Each assay consists of a primer set including of one pair of forward (FIP) and reverse (BIP) inner primers, forward (F3) and reverse (B3) outer primers. The assay may also include loop forward (LF) and/or loop back (LB) primers to accelerate the reaction. *Neisseria meningitides* serotypes A, B, C, Y and W135 can be detected using the assay of the invention.

2 Claims, 1 Drawing Sheet

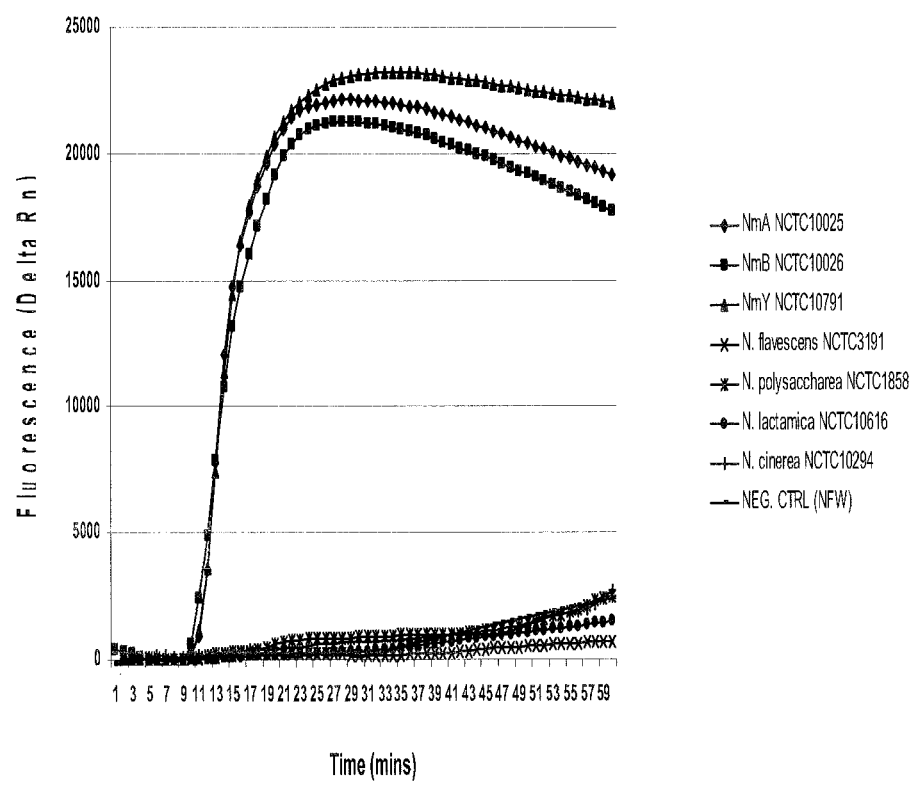

SEQUENCE LISTING

```
<160> NUMBER OF SEQ ID NOS: 69

<210> SEQ ID NO 1
<211> LENGTH: 45
<212> TYPE: DNA
<213> ORGANISM: Neisseria meningitidis

<400> SEQUENCE: 1
```

```
cgtctatggg tgcggtgggg agacgatctt gcaaaccgcc catac          45
```

<210> SEQ ID NO 2
<211> LENGTH: 48
<212> TYPE: DNA
<213> ORGANISM: Neisseria meningitidis

<400> SEQUENCE: 2

```
gtaaccacat caccgcgacg cagcatgtgc agctgacacg tggcaatg       48
```

<210> SEQ ID NO 3
<211> LENGTH: 18
<212> TYPE: DNA
<213> ORGANISM: Neisseria meningitidis

<400> SEQUENCE: 3

```
ccacgcgcat cagaacgg                                        18
```

<210> SEQ ID NO 4
<211> LENGTH: 21
<212> TYPE: DNA
<213> ORGANISM: Neisseria meningitidis

<400> SEQUENCE: 4

```
cggcaaatgt gcaggatacg a                                    21
```

<210> SEQ ID NO 5
<211> LENGTH: 19
<212> TYPE: DNA
<213> ORGANISM: Neisseria meningitidis

<400> SEQUENCE: 5

```
gcttatcgct ttctgaagc                                       19
```

<210> SEQ ID NO 6
<211> LENGTH: 20
<212> TYPE: DNA
<213> ORGANISM: Neisseria meningitidis

<400> SEQUENCE: 6

```
gcaactaaat cttccaaggc                                      20
```

<210> SEQ ID NO 7
<211> LENGTH: 42
<212> TYPE: DNA
<213> ORGANISM: Neisseria meningitidis

<400> SEQUENCE: 7

```
atcaccgcga cgcagcaaaa taagtacgaa ctgttgcctt gg              42
```

<210> SEQ ID NO 8
<211> LENGTH: 42
<212> TYPE: DNA
<213> ORGANISM: Neisseria meningitidis

<400> SEQUENCE: 8

```
acctttacgt ctatgggtgc ggaagcctct ygctgaaaaa cc              42
```

<210> SEQ ID NO 9
<211> LENGTH: 18
<212> TYPE: DNA
<213> ORGANISM: Neisseria meningitidis

<400> SEQUENCE: 9

-continued gctgacacgt ggcaatgt                                              18

<210> SEQ ID NO 10
<211> LENGTH: 20
<212> TYPE: DNA
<213> ORGANISM: Neisseria meningitidis

<400> SEQUENCE: 10
ccaatggctt cagaaagcga                                            20

<210> SEQ ID NO 11
<211> LENGTH: 41
<212> TYPE: DNA
<213> ORGANISM: Neisseria meningitidis

<400> SEQUENCE: 11
caaacacacc acgcgcatca gatctgaagc cattggccgt a                    41

<210> SEQ ID NO 12
<211> LENGTH: 42
<212> TYPE: DNA
<213> ORGANISM: Neisseria meningitidis

<400> SEQUENCE: 12
tgttccgcta tacgccattg gtactgccat aaccttgagc aa                   42

<210> SEQ ID NO 13
<211> LENGTH: 19
<212> TYPE: DNA
<213> ORGANISM: Neisseria meningitidis

<400> SEQUENCE: 13
agcyagaggc ttatcgctt                                             19

<210> SEQ ID NO 14
<211> LENGTH: 20
<212> TYPE: DNA
<213> ORGANISM: Neisseria meningitidis

<400> SEQUENCE: 14
ataccgttgg aatctctgcc                                            20

<210> SEQ ID NO 15
<211> LENGTH: 19
<212> TYPE: DNA
<213> ORGANISM: Neisseria meningitidis

<400> SEQUENCE: 15
cgatcttgca aaccgccca                                             19

<210> SEQ ID NO 16
<211> LENGTH: 22
<212> TYPE: DNA
<213> ORGANISM: Neisseria meningitidis

<400> SEQUENCE: 16
gcagaacgtc aggataaatg ga                                         22

<210> SEQ ID NO 17
<211> LENGTH: 18
<212> TYPE: DNA
<213> ORGANISM: Neisseria meningitidis

<400> SEQUENCE: 17

```
cgatcttgca aaccgccc                                                     18

<210> SEQ ID NO 18
<211> LENGTH: 40
<212> TYPE: DNA
<213> ORGANISM: Neisseria meningitidis

<400> SEQUENCE: 18
caaaccgccc atacggccaa atcggttttt cagcyagagg                             40

<210> SEQ ID NO 19
<211> LENGTH: 39
<212> TYPE: DNA
<213> ORGANISM: Neisseria meningitidis

<400> SEQUENCE: 19
aagatcgccg ttctgatgcg ccgttctgcc ggcaattcc                              39

<210> SEQ ID NO 20
<211> LENGTH: 18
<212> TYPE: DNA
<213> ORGANISM: Neisseria meningitidis

<400> SEQUENCE: 20
cggtggggag aacacaag                                                     18

<210> SEQ ID NO 21
<211> LENGTH: 20
<212> TYPE: DNA
<213> ORGANISM: Neisseria meningitidis

<400> SEQUENCE: 21
actgccataa ccttgagcaa                                                   20

<210> SEQ ID NO 22
<211> LENGTH: 23
<212> TYPE: DNA
<213> ORGANISM: Neisseria meningitidis

<400> SEQUENCE: 22
gtggtgtgtt tgtgttccgc tat                                               23

<210> SEQ ID NO 23
<211> LENGTH: 24
<212> TYPE: DNA
<213> ORGANISM: Neisseria meningitidis

<400> SEQUENCE: 23
gtggtgtgtt tgtgttccgc tata                                              24

<210> SEQ ID NO 24
<211> LENGTH: 38
<212> TYPE: DNA
<213> ORGANISM: Neisseria meningitidis

<400> SEQUENCE: 24
caccacgcgc atcagaacgg cagcyagagg cttatcgc                               38

<210> SEQ ID NO 25
<211> LENGTH: 41
<212> TYPE: DNA
<213> ORGANISM: Neisseria meningitidis

<400> SEQUENCE: 25
```

```
tgttccgcta tacgccattg gttgcctcac tgccataacc t              41
```

<210> SEQ ID NO 26
<211> LENGTH: 18
<212> TYPE: DNA
<213> ORGANISM: Neisseria meningitidis

<400> SEQUENCE: 26

```
cggtggggag aacacaag                                        18
```

<210> SEQ ID NO 27
<211> LENGTH: 20
<212> TYPE: DNA
<213> ORGANISM: Neisseria meningitidis

<400> SEQUENCE: 27

```
gcgcatcagc catattcaca                                      20
```

<210> SEQ ID NO 28
<211> LENGTH: 19
<212> TYPE: DNA
<213> ORGANISM: Neisseria meningitidis

<400> SEQUENCE: 28

```
cggccaatgg cttcagaaa                                       19
```

<210> SEQ ID NO 29
<211> LENGTH: 20
<212> TYPE: DNA
<213> ORGANISM: Neisseria meningitidis

<400> SEQUENCE: 29

```
ggaattgccg gcagaacgtc                                      20
```

<210> SEQ ID NO 30
<211> LENGTH: 19
<212> TYPE: DNA
<213> ORGANISM: Neisseria meningitidis

<400> SEQUENCE: 30

```
gaattgccgg cagaacgtc                                       19
```

<210> SEQ ID NO 31
<211> LENGTH: 40
<212> TYPE: DNA
<213> ORGANISM: Neisseria meningitidis

<400> SEQUENCE: 31

```
tccccaccgc acccatagac cggtgatgtg gttaccatga                40
```

<210> SEQ ID NO 32
<211> LENGTH: 40
<212> TYPE: DNA
<213> ORGANISM: Neisseria meningitidis

<400> SEQUENCE: 32

```
atcggttttt cagcyagagg ctttgcaaac cgcccatacg                40
```

<210> SEQ ID NO 33
<211> LENGTH: 19
<212> TYPE: DNA
<213> ORGANISM: Neisseria meningitidis

<400> SEQUENCE: 33
agttgcaaat ccgcgacaa                                        19

<210> SEQ ID NO 34
<211> LENGTH: 18
<212> TYPE: DNA
<213> ORGANISM: Neisseria meningitidis

<400> SEQUENCE: 34
cgcatcagaa cggcgatc                                         18

<210> SEQ ID NO 35
<211> LENGTH: 21
<212> TYPE: DNA
<213> ORGANISM: Neisseria meningitidis

<400> SEQUENCE: 35
atcgctttct gaagccattg g                                     21

<210> SEQ ID NO 36
<211> LENGTH: 20
<212> TYPE: DNA
<213> ORGANISM: Neisseria meningitidis

<400> SEQUENCE: 36
tcgctttctg aagccattgg                                       20

<210> SEQ ID NO 37
<211> LENGTH: 42
<212> TYPE: DNA
<213> ORGANISM: Neisseria meningitidis

<400> SEQUENCE: 37
gcgaatgcgc atcagccata tttgctcaag gttatggcag tg              42

<210> SEQ ID NO 38
<211> LENGTH: 40
<212> TYPE: DNA
<213> ORGANISM: Neisseria meningitidis

<400> SEQUENCE: 38
ttgtatgtgt cgaatgcgcc gtcggcgaga acacaaacga                 40

<210> SEQ ID NO 39
<211> LENGTH: 18
<212> TYPE: DNA
<213> ORGANISM: Neisseria meningitidis

<400> SEQUENCE: 39
gaattgccgg cagaacgt                                         18

<210> SEQ ID NO 40
<211> LENGTH: 18
<212> TYPE: DNA
<213> ORGANISM: Neisseria meningitidis

<400> SEQUENCE: 40
atactgttcg cgccactg                                         18

<210> SEQ ID NO 41
<211> LENGTH: 24
<212> TYPE: DNA
<213> ORGANISM: Neisseria meningitidis

<400> SEQUENCE: 41

-continued

| | |
|---|---|
| cacgatatac cgttggaatc tctg | 24 |

<210> SEQ ID NO 42
<211> LENGTH: 22
<212> TYPE: DNA
<213> ORGANISM: Neisseria meningitidis

<400> SEQUENCE: 42

| | |
|---|---|
| tggctgaagt gcagaaattc tt | 22 |

<210> SEQ ID NO 43
<211> LENGTH: 24
<212> TYPE: DNA
<213> ORGANISM: Neisseria meningitidis

<400> SEQUENCE: 43

| | |
|---|---|
| acacgatata ccgttggaat ctct | 24 |

<210> SEQ ID NO 44
<211> LENGTH: 23
<212> TYPE: DNA
<213> ORGANISM: Neisseria meningitidis

<400> SEQUENCE: 44

| | |
|---|---|
| tggctgaagt gcagaaattc ttg | 23 |

<210> SEQ ID NO 45
<211> LENGTH: 40
<212> TYPE: DNA
<213> ORGANISM: Neisseria meningitidis

<400> SEQUENCE: 45

| | |
|---|---|
| ccatcacttg tggctgattg gcggtcggta aaacgcctgg | 40 |

<210> SEQ ID NO 46
<211> LENGTH: 40
<212> TYPE: DNA
<213> ORGANISM: Neisseria meningitidis

<400> SEQUENCE: 46

| | |
|---|---|
| ggcgaatgtg tcggtgattc gtgcatccaa cacacgctca | 40 |

<210> SEQ ID NO 47
<211> LENGTH: 18
<212> TYPE: DNA
<213> ORGANISM: Neisseria meningitidis

<400> SEQUENCE: 47

| | |
|---|---|
| tgccgtttgt tggcgata | 18 |

<210> SEQ ID NO 48
<211> LENGTH: 20
<212> TYPE: DNA
<213> ORGANISM: Neisseria meningitidis

<400> SEQUENCE: 48

| | |
|---|---|
| cacatttgcc gttgaaccac | 20 |

<210> SEQ ID NO 49
<211> LENGTH: 38
<212> TYPE: DNA
<213> ORGANISM: Neisseria meningitidis

<400> SEQUENCE: 49
ggcgttttac cgaccaccga ggcacgtggt acggtttc                                    38

<210> SEQ ID NO 50
<211> LENGTH: 40
<212> TYPE: DNA
<213> ORGANISM: Neisseria meningitidis

<400> SEQUENCE: 50
aggccgcctg aaaaaaatgg ccgacacatt cgccgcatta                                  40

<210> SEQ ID NO 51
<211> LENGTH: 18
<212> TYPE: DNA
<213> ORGANISM: Neisseria meningitidis

<400> SEQUENCE: 51
agttgccaga gcagttgg                                                          18

<210> SEQ ID NO 52
<211> LENGTH: 19
<212> TYPE: DNA
<213> ORGANISM: Neisseria meningitidis

<400> SEQUENCE: 52
cgcacactat tcccagcac                                                         19

<210> SEQ ID NO 53
<211> LENGTH: 38
<212> TYPE: DNA
<213> ORGANISM: Neisseria meningitidis

<400> SEQUENCE: 53
caccacgcgc atcagaacgg cagcyagagg cttatcgc                                    38

<210> SEQ ID NO 54
<211> LENGTH: 41
<212> TYPE: DNA
<213> ORGANISM: Neisseria meningitidis

<400> SEQUENCE: 54
tgttccgcta tacgccattg gttgcctcac tgccataacc t                                41

<210> SEQ ID NO 55
<211> LENGTH: 18
<212> TYPE: DNA
<213> ORGANISM: Neisseria meningitidis

<400> SEQUENCE: 55
cggtggggag aacacaag                                                          18

<210> SEQ ID NO 56
<211> LENGTH: 20
<212> TYPE: DNA
<213> ORGANISM: Neisseria meningitidis

<400> SEQUENCE: 56
gcgcatcagc catattcaca                                                        20

<210> SEQ ID NO 57
<211> LENGTH: 19
<212> TYPE: DNA
<213> ORGANISM: Neisseria meningitidis

<400> SEQUENCE: 57
cggccaatgg cttcagaaa                                           19

<210> SEQ ID NO 58
<211> LENGTH: 20
<212> TYPE: DNA
<213> ORGANISM: Neisseria meningitidis

<400> SEQUENCE: 58
ggaattgccg gcagaacgtc                                          20

<210> SEQ ID NO 59
<211> LENGTH: 41
<212> TYPE: DNA
<213> ORGANISM: Neisseria meningitidis

<400> SEQUENCE: 59
ggccattttt ttcaggcggc cttggcgata tttcggtggt c                  41

<210> SEQ ID NO 60
<211> LENGTH: 40
<212> TYPE: DNA
<213> ORGANISM: Neisseria meningitidis

<400> SEQUENCE: 60
caagtgatgg tgcgtttggt gcagcggcat acgcacacta                    40

<210> SEQ ID NO 61
<211> LENGTH: 19
<212> TYPE: DNA
<213> ORGANISM: Neisseria meningitidis

<400> SEQUENCE: 61
acgtggtacg gtttctgtg                                           19

<210> SEQ ID NO 62
<211> LENGTH: 18
<212> TYPE: DNA
<213> ORGANISM: Neisseria meningitidis

<400> SEQUENCE: 62
ccaccgcatc caacacac                                            18

<210> SEQ ID NO 63
<211> LENGTH: 39
<212> TYPE: DNA
<213> ORGANISM: Neisseria meningitidis

<400> SEQUENCE: 63
caacacacgc tcaccggctg ggcgaatgtg tcggtgatt                     39

<210> SEQ ID NO 64
<211> LENGTH: 40
<212> TYPE: DNA
<213> ORGANISM: Neisseria meningitidis

<400> SEQUENCE: 64
gcggtaggtg gttcaacggc actacattgc cacgtgtcag                    40

<210> SEQ ID NO 65
<211> LENGTH: 18
<212> TYPE: DNA
<213> ORGANISM: Neisseria meningitidis

<400> SEQUENCE: 65

-continued

```
ggtgcgtttg gtgcagaa                                                  18

<210> SEQ ID NO 66
<211> LENGTH: 19
<212> TYPE: DNA
<213> ORGANISM: Neisseria meningitidis

<400> SEQUENCE: 66
ttccaaggca acagttcgt                                                 19

<210> SEQ ID NO 67
<211> LENGTH: 21
<212> TYPE: DNA
<213> ORGANISM: Neisseria meningitidis

<400> SEQUENCE: 67
cgtgctggga atagtgtgcg t                                              21

<210> SEQ ID NO 68
<211> LENGTH: 21
<212> TYPE: DNA
<213> ORGANISM: Neisseria meningitidis

<400> SEQUENCE: 68
atgtgcagga tacgaatgtg c                                              21

<210> SEQ ID NO 69
<211> LENGTH: 21
<212> TYPE: DNA
<213> ORGANISM: Neisseria meningitidis

<400> SEQUENCE: 69
ggsaatagtg tgcgtatgcc g                                              21
```

DETECTION OF *NEISSERIA MENINGITIDIS* BY LOOP MEDIATED ISOTHERMAL AMPLIFICATION

ASSAY

The present invention relates to a test for meningitis. More specifically the invention relates to a near bedside assay for *Neisseria meningitidis*.

The pathogenic bacterium *Neisseria meningitidis* (NMG) is a major worldwide cause of invasive bacterial meningitis and septicaemia, known as 'meningococcal disease' (MD). Although relatively rare in developed countries (1-3 cases per 100,000 population per year), MD has serious consequences for those who are affected, especially children. Vaccination has reduced the incidence of MD in recent years, although no effective vaccine is available for Group B NMG, which causes >40% of UK cases. MD has a mortality rate of between 15% (meningococcal meningitis) and 50% (meningococcal septicaemia), despite the availability of effective antibiotic therapy. This is partly because of difficulty with diagnosis of early-stage MD, which can lead to delayed diagnosis.

Diagnosis of MD currently relies entirely on correct interpretation of clinical symptoms, which are frequently absent or equivocal. This makes clinical diagnosis challenging, especially in very young children, and there is no reliable diagnostic test available to assist physicians with making a diagnosis of early-stage MD. Existing laboratory tests for NMG infection involve either conventional isolation and culture—which takes too long to be useful as part of a clinical diagnosis, or 'polymerase chain reaction' (PCR) tests—which can also be time-consuming, and are often available only in reference laboratory settings. The most rapid current test to detect NMG (gene-specific PCR) is not available in most hospital bacteriology laboratories, due to lack of expertise/specialist equipment for molecular diagnostic testing. For this reason, the currently available tests are used only to confirm a clinical diagnosis of MD.

The consequences of delayed diagnosis for the patient can be catastrophic—leading to permanent disability (often in the form of serious neurological damage or multiple limb amputations) or death. There is a clear need for a rapid and reliable molecular diagnostic test, offering high positive predictive value (PPV) and negative predictive value (NPV) to assist with diagnosis of early-stage MD. Most importantly, a test which could be applied either at the point of care, or in a near-patient setting, and which gave a rapid result (1-2 hours) would provide physicians with timely information which is currently only useful to confirm a diagnosis

*Neisseria meningitidis* is a major cause of bacterial meningitis and septicaemia worldwide. Early diagnosis of meningococcal disease (MD) is difficult because the initial presenting features are common to those of simple upper respiratory tract infection such as coryza and sore throat. Delayed diagnosis of MD can have catastrophic consequences for the patient, and contributes to the high levels of morbidity and mortality which can be associated with MD, especially in children. The classical features of MD, which include haemorrhagic rash, meningism and reduced level of consciousness, may come on rapidly but still relatively late (e.g. 12-24 hours) after the first symptoms of the illness start. A recent study (reference 1) has suggested that leg pains, cold extremities and abnormal skin colour are seen in the first 12 hours of MD. However, the positive and negative predictive value of these signs is not known, and these symptoms are likely to be present in children with other infections such as influenza. Similar difficulties also surround early clinical diagnosis of meningitis and septicaemia caused by other bacteria, especially *Streptococcus pneumoniae*. Significantly, there is no reliable test to assist clinicians with diagnosis of early-stage MD; diagnosis can be made only on the basis of clinical symptoms, with inevitably serious consequences if these symptoms are absent or overlooked.

Laboratory-based molecular tests are currently not useful as diagnostic tools (except for confirming a diagnosis) because laboratory turn around times can be significant, even for the fastest tests. The transport time between specimen collection and laboratory testing also has a significant adverse effect on positivity rates for confirmatory MD molecular assays (reference 2), leading to false-negative test results. While laboratory culture of *N. meningitidis* has historically been the gold standard for confirming diagnosis of MD, pre-admission antibiotic therapy has greatly reduced the value of routine culture, and the time required (24-48 hours) generally limits its role to confirming antibiotic susceptibility in culture-positive specimens. Data from a previous study in our laboratory (reference 3) illustrates the very low success rate of culture in confirming diagnosis of MD.

In view of these problems, a rapid and reliable molecular diagnostic test, offering high positive predictive value (PPV) and negative predictive value (NPV), would be extremely useful. Most importantly, a test which could be applied either at the point of care, or in a near-patient setting, and which gave a rapid result (1-2 hours) could avoid the critical delays which are associated with submitting a specimen for laboratory testing. This would assist clinicians by providing information which is currently only available to confirm a diagnosis of MD.

A number of molecular tests for laboratory detection of *N. meningitidis* have been described in the literature. These tests generally rely on the Polymerase Chain Reaction (PCR) to amplify and detect virulence genes, and focus on identification of cultured *N. meningitidis* isolates (references 4 & 5) or detection using invasive specimens such as blood or cerebrospinal fluid (references 6 & 7). In the course of a recent research project investigators demonstrated an effective combined PCR laboratory assay which detects two important virulence genes from *N. meningitidis* in nose and throat swab specimens (Dr. K. Dunlop, MD Thesis; reference 3). This assay proved to be very effective for confirming diagnosis of MD in a case-control clinical trial (n=104 suspected cases, n=104 case controls), which showed that the test has high sensitivity (81%), specificity (100%), PPV (100%) and NPV (92%). The study clearly showed that these gene targets are useful diagnostic biomarkers of MD, and they can be easily detected in non-invasive clinical specimens. Current recommendations from the Chief Medical Officer include taking blood samples for PCR analysis and nose/throat swabs for culture only. Published PHLS guidelines (reference 8) note that molecular testing of throat swab specimens is effective, although they do not consider this to be 'definitively diagnostic' for confirmatory testing by reference laboratories at present. Nevertheless, recent data strongly suggest that the use of combined molecular testing directly on nasal and pharyngeal swab specimens has considerable potential for improving the diagnosis of MD in this hospital and elsewhere.

While PCR assays are clearly a valuable laboratory diagnostic method, it would not be practical to apply these tests in a near-patient setting, as they require both laboratory skills and specialised instruments (a thermal cycler and gel electrophoresis equipment, or a 'real-time' PCR instrument).

It is an aim of the present invention to develop a test which detects the same gene targets as the current PCR assay, but using an alternative 'isothermal' DNA amplification technique, in a format which would be practical for near-patient testing by staff without specialised laboratory skills.

It is an aim of the present invention to provide a rapid qualitative molecular test to detect *Neisseria meningitidis* DNA in patient specimens, allowing rapid confirmation of meningococcal infection.

There is currently no rapid diagnostic test which can be used to assist with clinical diagnosis of early-stage meningococcal disease, and significant turnaround times are required even for the fastest laboratory tests. In contrast, the proposed new test would be available for near-patient testing by staff without laboratory skills and without highly specialized or costly equipment (i.e. it could be used in hospital A&E/E.R. departments, large primary care units or pharmacies).

According to the present invention there is provided a diagnostic test for meningococcal disease, the test comprising nucleic acid primer sets capable of detecting *Neisseria meningitides* in a LAMP based molecular test, the primer set being chosen from the primer sets listed in Table 1 as LAMP SETS 1 to 12 comprising a set of SEQUENCE IDs selected from ID:1 to ID:69.

A LAMP primer set consists of one pair of forward (FIP) and reverse (BIP) inner primers, forward (F3) and reverse (B3) outer primers. FIP, BIP, F3 & B3 primers are essential for amplification to proceed. The addition of loop forward (LF) and/or loop back (LB) primers significantly accelerates amplification reducing overall detection times by 50%

The invention also provides any of the primers as set out in Table 1 as Sequence ID:1 through Sequence ID:69, individually or in combination with any of the other listed primers for use in an assay for *Neisseria meningitides*.

Preferably the assay is a LAMP assay.

Preferred primer sets are chosen from the group consisting of LAMP SETS 1, 3, 5, 6, 7 and 12.

Particularly preferred primers sets are 3, 5, 1, 7, 12 and 6.

In a preferred embodiment of the invention the primer set is chosen from LAMP primer sets 3 or 5 as shown in Table 1.

The nomenclature used herein to describe the primer sequences for preferred LAMP sets is as follows. L3L3 refers to LAMP set 3 (FIP, BIP, F3 & B3) and loop set 3 i.e.—Seq IDs 11 to 14 and 16 and 17. L3L1 refers to LAMP set 3 (FIP, BIP, F3 & B3) and loop set 1 i.e.—Seq IDs 11 to 14 and 15 and 16. In each case the first 4 sequences are essential and the additional two loop primers accelerate the reaction.

Preferably the LAMP primer set comprises SET 3 (L3L3) consisting of Seq IDs 11 to 14 and IDs 16 and 17.

An alternative preferred primer set comprises SET 3 (L3L1) consisting of Seq IDs 11 to 16.

Another preferred primer set comprises SETS (L5L1) consisting of Seq IDs 24 to 29.

The preferred primer sets are listed in Table 2

The invention therefore provides the use of the listed primers in a diagnostic test for *Neisseria meningitides*.

The invention will be further described with reference to the following experimental details and with reference to the accompanying FIGURE wherein FIG. 1 illustrates Real Time ctrA LAMP plot total fluorescence against time in mins. for *Neisseria meningitidis* serogroups A NCTC10025, serogroup B NCTC10026, serogroup Y NCTC10791, *Neisseria flavescens* NCTC 3191, *Neisseria polysaccharea* NCTC1858, *Neisseria lactamica* NCTC 10616, *Neisseria cinerea* NCTC 10294 total nucleic acid extracts & No Template Control (Nuclease Free Water)

The exemplification of the utility of the invention involves consecutive phases:
- Phase 1—Assay development and laboratory optimisation
- Phase 2—Transfer of the assay to a 'near patient' clinical setting
- Phase 3—Clinical validation of the near-patient assay
- Phase 4—Data analysis and reporting Phase 1—Assay Development and Laboratory Optimisation Target Selection and Assay Design:

The proposed test detects the same gene targets as the existing PCR assay. These are: ctrA, encoding a capsule polysaccharide export outer membrane protein; and porA, encoding a separate outer membrane protein. The products of these genes are important virulence determinants in *N. meningitidis*, and the inventor's data demonstrates that the conserved regions within these genes are useful biomarkers of MD.

It would not be practical to apply existing PCR tests in a near-patient setting so the inventors have developed a test which detects the same targets, but uses an alternative 'isothermal' DNA amplification technique. Unlike PCR, isothermal methods do not require expensive or complicated thermal cycling instruments, which makes them very attractive for point-of-care or near-patient testing. An isothermal technique called 'Loop-mediated Isothermal Amplification' (LAMP), used both in laboratory and near-patient settings has distinct advantages over the current PCR laboratory test.

The LAMP method (references 9, 10 & 11) is a type of 'strand displacement' amplification, which utilises a specially designed set of oligonucleotide primers, and a specific thermophilic DNA polymerase derived from *Bacillus stearothermophilus*. The primers are designed to promote the formation of 'hairpin-loop' structures during the initial stages of the reaction, allowing high levels of self-primed DNA synthesis to occur from these structures as the reaction continues. In brief, the reaction is initiated by annealing and extension of a pair of 'loop-forming' primers, followed by annealing and extension of a pair of flanking primers. Extension of these primers results in strand-displacement of the loop-forming elements, which fold up to form terminal hairpin-loop structures. Once these key structures have appeared, the amplification process becomes self-sustaining, and proceeds at 60-65 degrees C. in a continuous and exponential manner (rather than a cyclic manner, like PCR) until all of the nucleotides (dATP, dTTP, dCTP & dGTP) in the reaction mixture have been incorporated into the amplified DNA. LAMP allows amplification of target DNA sequences with higher sensitivity and specificity than PCR, often with reaction times of below 30 minutes, which is equivalent to the fastest real-time PCR tests. The target sequence which is amplified is typically 200-300 base-pairs (bp) in length, and the reaction relies upon recognition of between 120 bp and 160 bp of this sequence by several primers simultaneously during the amplification process. This high level of stringency makes the amplification highly specific, such that the appearance of amplified DNA in a reaction occurs only if the entire target sequence was initially present. While characterisation of the amplified DNA (on the basis of its restriction pattern or DNA sequence) is possible, this is generally not necessary as the reaction is so specific; the presence of amplified DNA indicates that the target sequence was present. Significantly, the yield of amplified target DNA in positive reactions is so high, it can be easily and directly detected in the reaction tube (references 12 & 13) allowing rapid discrimination between positive and negative specimens.

A number of diagnostic LAMP assays have been described in the literature, including tests to detect causes of viral meningitis such as mumps virus (using RT-LAMP; reference 14) and human herpes virus 7 (HHV-7; reference 15). The published HHV-7 LAMP assay was clinically validated, and used to detect primary HHV-7 infection in serum samples in a 60 minute assay. Although there is growing interest in the use of LAMP to develop rapid diagnostic tests, no studies using LAMP to detect *N. meningitidis* have been published to date.

The very high sensitivity of LAMP may allow the initial DNA extraction step during the assay to be avoided, allowing a diluted specimen lysate to be used instead of purified DNA. This has the potential to further reduce the total time required to complete the test, as the extraction stage forms an increasingly large proportion of the total assay time as faster amplification and detection methods are employed. A published allele-specific LAMP assay for human cytochrome P450 'single nucleotide polymorphism' genotyping (reference 17) has been used to selectively amplify target sequences from whole-blood lysates, which suggests that this approach is viable. The P450 study also demonstrated that LAMP can be used to discriminate between closely related genotypes, which is relevant for the *N. meningitidis* genotyping test (using the siaD gene) proposed here.

The inventors have now developed a prototype LAMP assay which can detect the *N. meningitidis* ctrA gene target in extracted clinical specimens in 60 minutes using LAMP primers as set out in Table 1.

This initial part of the project involved detailed gene sequence analysis, followed by the design and testing of a range of LAMP primer sets. The laboratory performance of each set has been examined, and the most effective and practical primers selected for transfer to a clinical setting (Phase 2) and clinical validation (Phase 3).

The designed primer sets are set out in Table 1 and identified as LAMP SETS 1 to 12 consisting of primers being sequence ID:1 through to sequence ID:69, together with an indication of their effectiveness with different strains.

Assay Optimisation and Laboratory Validation:

The principal objective of this part of the study is an optimised and robust test which will be useable by a member of staff with minimal technical training. This work will compare LAMP with the existing nested PCR test method, and will focus on the ctrA and porA targets, with the siaD and lytA targets as secondary objectives. Laboratory validation work will include:

Optimisation of the LAMP reaction conditions (by varying the reagent composition, incubation temperature, reaction time etc.).

Preparation of control and reference material (i.e. cloned reference targets).

Determination of the analytical sensitivity of the test (using reference materials).

Determination of clinical sensitivity (using 'spiked' and real clinical samples).

Specificity testing, using typed *N. meningitidis* strains, other clinically relevant bacteria, and human genomic DNA. The specificity panel will include NCMBI reference strains from 9 serogroups known to cause invasive disease (A, B, Cl+, Cl−, X, Y, W-135, Z & L) and clinical isolates from this hospital. Identification of clinical isolates will be confirmed by 16S sequencing.

Comparison of test performance using fresh vs. stored specimens.

A major objective is to understand possible sources of false-positive and false-negative results, in order to maximize the PPV and NPV of the test. A positive control LAMP assay will also be developed, allowing control reactions to be included with every batch of unknowns. Phage Lambda DNA will be used as a control target, as this is readily available, easily standardized, and will not interfere or cross-react with detection of any of the intended target genes.

As an additional benefit of this project, it should be noted that the optimised and laboratory-validated tests will be immediately useful for rapid identification of *N. meningitidis* and *S. pneumoniae* isolates as part of the routine clinical microbiology service in this hospital, and elsewhere.

Real-Time Detection Methods:

Real-time detection of amplified DNA during LAMP reactions is possible, using three different methods: by turbidometry (detection of insoluble magnesium pyrophosphate accumulation in reactions), by ethidium bromide fluorescence, or by SYBR Green I fluorescence (which both detect accumulation of double-stranded DNA in reactions). Real-time monitoring increases the complexity of the test/instrument format required, as some form of optical or fluorescence measurement must be used. However, this is offset by the fact that provisional positive results may be obtained much more quickly (i.e. as soon as an amplified product is detected in a reaction). Detectable amounts of DNA may be synthesised in a little as 15 minutes in LAMP reactions (reference 18) and in some cases the positive reaction can even be visualized by eye.

Following the assay optimisation stage, the proposed project will also assess the available real-time monitoring methods, to see whether they could usefully be incorporated into a near-patient test.

Extraction Methods:

An important part of the study will be the development of a rapid DNA extraction method which can be used for near-patient testing. Current laboratory protocols for DNA extraction are too cumbersome for use in near-patient settings, so a simpler method involving specimen lysis and dilution will also be developed, using both PCR and the optimised LAMP test to assess performance. The inventors are investigating whether the use of crude specimen lysates for molecular assays is feasible, in order to simplify the process further, and to minimise the specimen processing time required.

Sequencing:

Some DNA sequencing work is being conducted for two reasons:
  i) to confirm the taxonomic position of *N. meningitidis* isolates obtained during the study, and previously isolated reference strains (by 16S rDNA sequencing). This will rule out misidentification of the putative pathogen in cases where near-patient and/or laboratory molecular tests to detect *N. meningitidis* prove to be negative.
  ii) to increase the number of ctrA, porA and siaD sequences in the database. This will allow more detailed sequence analysis to be undertaken, and the design of primer sets to be refined further, especially for genotyping purposes.

Only the optimised *N. meningitidis* ctrA and porA LAMP assays will be used for subsequent near-patient testing.

Phase 2—Transfer of (ctrA and porA) Tests to Near-Patient Setting

Protocol Development:

Some additional method development is expected, both to deliver a usable near-patient testing protocol, and for the comparative laboratory testing protocols. In particular, the issues surrounding specimen collection and processing will be addressed at this stage, and detailed 'standard operating procedures' will be written. All specimens will be subjected to culture through the routine bacteriology service, and specimens will be processed in parallel using the previously developed PCR assay and the optimised near-patient method in a laboratory setting, for comparison.

Training:

As a central objective of the proposed work is to develop a test which can be used by non-laboratory staff, appropriate training, supervision and mentoring will be provided for the non-technical staff (research nurses) who will conduct the test in a near-patient setting. The high sensitivity of molecular tests makes them susceptible to contamination by amplified test products, which can lead to false-positive results. An important part of the training will be to ensure that the staff involved understand the issues surrounding contamination, and can avoid contamination of the near-patient testing area. The final assay will incorporate negative control reactions at all stages so that contamination problems can be quickly identified and addressed.

Pre-Clinical Validation:

Pre-clinical validation of the optimised test will be essential to assess the performance of assay in a near-patient setting. This phase will therefore conclude with blinded and randomized processing of a number of spiked and control specimens, to confirm that the new protocols can be used as anticipated.

Phase 3—Clinical Validation

Study Design: Modified Case-Control.

Patient Groups

Group 1: All children with suspected meningococcal disease (MD) are entered into a 'clinical care pathway' and have a standardised set of investigations (to make diagnosis, assessment of severity and initial treatment) performed. In the recently completed one year study in the inventors' unit, 104 suspected MD children were recruited in 12 months and over 33% had proven MD (clinical picture PLUS blood culture +ve or +ve meningococcal PCR at Manchester Reference Laboratory). The inventors will perform a case control study over at least a 2½ year period. The new test (measured from a combined nasal and throat swab, and blood) would be applied to all children with suspected MD entering the MD care pathway (estimated N=250 children) over this period (giving about 80 definite cases). This group of children is already 'filtered as possible cases of MD'. The inventors want to be sure that the newly developed test has a high sensitivity. If the true sensitivity were 90% then a study of 80 affected children would give an estimate of the sensitivity with 95% exact confidence intervals of width no wider than 81% to 95%. Children entered into this group would include those in whom the A&E doctor considered might possibly have MD (fever, petechial rash or signs of meningism and those with signs of possible septicaemia—eg. features of circulatory failure). These children routinely have a 'meningococcal pack' performed (blood cultures, serology, PCR for reference laboratory, blood count and ESR, CRP) and a nasal and pharyngeal swab taken for PCR and culture. In this study an additional combined nasal and throat swab will be taken from every child entered into this MD care pathway.

Group 2: The inventors want their newly developed test (assessed on a combined nasal and throat swab, and blood where possible) to have a very high specificity/NPV. If the true specificity was 98% then a study of 750 unaffected children would give an estimate of the specificity with 95% exact confidence intervals of width no wider than 97% to 99%. They plan to study 750 children attending the A&E department with non-specific febrile or upper respiratory tract illnesses who are not being entered into the meningococcal care pathway.

Included in this group will be children with;
i] simple febrile illnesses with features of a head cold (excluding children with classical respiratory infections eg 'croup')
ii] non-specific fevers including those with leg pains, cold hands and feet but who are not considered to be 'ill' to enter into the MD care pathway which could include those with early features of sepsis. Such patients were described recently as risk factors for early MD (Reference 1) but the frequency of these symptoms in the non-meningitis population is not known. A combined throat and nasal swab for the new MD test will be taken from these children by the researchers, along with a blood sample, where this is possible. As most of these children will likely be sent home from A&E a follow-up telephone call will be made 24, 48 and 72 hours after recruitment to determine the natural resolution (or not) of the illness.

In conclusion design and testing of new LAMP primer sets has been developed and the results are shown in detail in Table 1. LAMP reactions will be optimized together with development of rapid extraction protocols for clinical specimens (nasal and pharyngeal swabs).

Comparison of LAMP and PCR assays with respect to specificity, analytical/clinical sensitivity, time-to-result, and practicality for near-patient use, using both standard and rapid extraction protocols will be undertaken to demonstrate rapid and robust laboratory validated assays which can detect the target genes with high specificity and known analytical sensitivity.

This invention will provide rapid laboratory assays for *N. meningitidis* detection and genotyping, and rapid diagnostic tests for detection of *N. meningitidis* in non-invasive specimens, validated in both laboratory and clinical settings, which will be effective enough to be widely adopted in near-patient settings.

A LAMP assay to detect the lytA gene (encoding the protein autolysin) from *Streptococcus pneumoniae*, has been described previously (reference 16). This laboratory assay was shown to detect *S. pneumoniae* DNA with high specificity, and a sensitivity $10^3$ times higher than conventional single-round PCR. As a secondary objective, the inventors propose to validate this published assay in the laboratory alongside the new test during this study, for testing of ctrA and porA negative specimens. This will also enable them to collect preliminary data on whether molecular detection of *S. pneumoniae* in nasal or throat swab specimens might correlate with diagnosis of pneumococcal meningitis or septicaemia in the study group.

Results

LAMP Primer Design

Oligonucleotide primers specific for *N. meningitidis* ctrA gene were designed corresponding to recognised conserved genomic regions (Positions in ctrA gene AF520902.1) using online LAMP primer design software Primer Explorer version 3.0 available at http://loopamp.eiken.co.jp/e/lamp/primer.html (NB. LAMP & LOOP primer set ID: 1 was designed by one of the inventors without aid of software). A LAMP primer set consisted of one pair of forward (FIP) and reverse (BIP) inner primers, forward (F3) and reverse (B3) outer primers. FIP, BIP, F3 & B3 primers are essential for amplification to proceed. The addition of loop forward (LF) and/or loop back (LB) primers significantly accelerates amplification reducing overall detection times by 50% (Nagamine, et al, 2002) and this was confirmed by data generated in the inventors' laboratory. With certain LAMP primer sets it was possible to design only Loop back (LB) primers (eg. LAMP6, LAMP4) and for others no forward or back Loop primers could be designed. See Table 1 for list of primer sets.

The primers are designed to promote the formation of 'hairpin-loop' structures during the initial stages of the reaction, allowing high levels of self-primed DNA synthesis to occur from these structures as the self sustaining reaction proceeds (Notomi, et al, 2000). A by-product of LAMP reactions is magnesium pyrophosphate which can be measured by turbidity/fluorescence endpoint or in Real Time (Tomita, et al, 2008). Animation of the reaction (minus loop primers) can be seen at http://loopamp.eiken.co.jp/e/lamp/anim.html and the loop principle is outlined by Nagamine, et al, 2002 and at http://loopamp.eiken.co.jp/e/lamp/loop.html.

Neisseria meningococcus ctrA LAMP Primer Sets

All primer sets designed using LAMP software July 2007, except ID:1 designed March 2006). Core sequences shown in bold.

Primers: FIP=forward inner; BIP=backward inner; F3=forward outer; B3=backward outer; LF=loop forward; LB=loop backward.

Positions in ctrA Gene AF520902.1

TABLE 1 ctrA LAMP primer sets and Sequence ID numbers.

| ctrA LAMP SET | PRIMER SEQ ID | | SEQUENCE 5' - 3' |
|---|---|---|---|
| SET 1 | ID1 | FIP | CGTCTATGGGTGCGGTGGGGAGACGATCTTGCAAACCGCCCATAC |
| | ID2 | BIP | GTAACCACATCACCGCGACGCAGCATGTGCAGCTGACACGTGGCAATG |
| | ID3 | F3 | CCACGCGCATCAGAACGG |
| | ID4 | B3 | CGGCAAATGTGCAGGATACGA |
| | ID5 | LF1 | GCTTATCGCTTTCTGAAGC |
| | ID6 | LB1 | GCAACTAAATCTTCCAAGGC |
| SET 2 | ID7 | FIP | ATCACCGCGACGCAGCAAAATAAGTACGAACTGTTGCCTTGG |
| | ID8 | BIP | ACCTTTACGTCTATGGGTGCGGAAGCCTCTYGCTGAAAAACC |
| | ID9 | F3 | GCTGACACGTGGCAATGT |
| | ID10 | B3 | CCAATGGCTTCAGAAAGCGA |
| SET 3 | ID11 | FIP | CAAACACACCACGCGCATCAGATCTGAAGCCATTGGCCGTA |
| | ID12 | BIP | TGTTCCGCTATACGCCATTGGTACTGCCATAACCTTGAGCAA |
| | ID13 | F3 | AGCYAGAGGCTTATCGCTT |
| | ID14 | B3 | ATACCGTTGGAATCTCTGCC |
| | ID15 | LF1 | CGATCTTGCAAACCGCCCA |
| | ID16 & LB3 | LB1 | GCAGAACGTCAGGATAAATGGA |
| | ID17 | LF3 | CGATCTTGCAAACCGCCC |
| SET 4 | ID18 | FIP | CAAACCGCCCATACGCCAAATCGGTTTTTCAGCYAGAGG |
| | ID19 | BIP | AAGATCGCCGTTCTGATGCGCCGTTCTGCCGGCAATTCC |
| | ID20 | F3 | CGGTGGGGAGAACACAAG |
| | ID21 | B3 | ACTGCCATAACCTTGAGCAA |
| | ID22 | LB1 | GTGGTGTGTTTGTGTTCCGCTAT |
| | ID23 | LB2 | GTGGTGTGTTTGTGTTCCGCTATA |
| SET 5 | ID24 | FIP | CACCACGCGCATCAGAACGGCAGCYAGAGGCTTATCGC |
| | ID25 | BIP | TGTTCCGCTATACGCCATTGGTTGCCTCACTGCCATAACCT |
| | ID26 | F3 | CGGTGGGGAGAACACAAG |
| | ID27 | B3 | GCGCATCAGCCATATTCACA |
| | ID28 & LF3 | LF1 | CGGCCAATGGCTTCAGAAA |
| | ID29 | LB1 | GGAATTGCCGGCAGAACGTC |
| | ID30 | LB3 | GAATTGCCGGCAGAACGTC |
| SET 6 | ID31 | FIP | TCCCCACCGCACCCATAGACCGGTGATGTGGTTACCATGA |
| | ID32 | BIP | ATCGGTTTTTCAGCYAGAGGCTTTGCAAACCGCCCATACG |
| | ID33 | F3 | AGTTGCAAATCCGCGACAA |
| | ID34 | B3 | CGCATCAGAACGGCGATC |
| | ID35 | LB1 | ATCGCTTTCTGAAGCCATTGG |
| | ID36 | LB2 | TCGCTTTCTGAAGCCATTGG |

TABLE 1 -continued ctrA LAMP primer sets and Sequence ID numbers.

| ctrA LAMP SET | PRIMER SEQ ID | | SEQUENCE 5' - 3' |
|---|---|---|---|
| SET 7 | ID37 | FIP | GCGAATGCGCATCAGCCATATTTGCTCAAGGTTATGGCAGTG |
| | ID38 | BIP | TTGTATGTGTCGAATGCGCCGTCGGCGAGAACACAAACGA |
| | ID39 | F3 | GAATTGCCGGCAGAACGT |
| | ID40 | B3 | ATACTGTTCGCGCCACTG |
| | ID41 & LF2 | LF1 | CACGATATACCGTTGGAATCTCTG |
| | ID42 | LB1 | TGGCTGAAGTGCAGAAATTCTT |
| | ID43 | LF6 | ACACGATATACCGTTGGAATCTCT |
| | ID44 & LB6 | LB2 | TGGCTGAAGTGCAGAAATTCTTG |
| SET 8 | ID45 | FIP | CCATCACTTGTGGCTGATTGGCGGTCGGTAAACGCCTGG |
| | ID46 | BIP | GGCGAATGTGTCGGTGATTCGTGCATCCAACACACGCTCA |
| | ID47 | F3 | TGCCGTTTGTTGGCGATA |
| | ID48 | B3 | CACATTTGCCGTTGAACCAC |
| SET 9 | ID49 | FIP | GGCGTTTTACCGACCACCGAGGCACGTGGTACGGTTTC |
| | ID50 | BIP | AGGCCGCCTGAAAAAAATGGCCGACACATTCGCCGCATTA |
| | ID51 | F3 | AGTTGCCAGAGCAGTTGG |
| | ID52 | B3 | CGCACACTATTCCCAGCAC |
| SET 10 | ID53 | FIP | CACCACGCGCATCAGAACGGCAGCYAGAGGCTTATCGC |
| | ID54 | BIP | TGTTCCGCTATACGCCATTGGTTGCCTCACTGCCATAACCT |
| | ID55 | F3 | CGGTGGGGAGAACACAAG |
| | ID56 | B3 | GCGCATCAGCCATATTCACA |
| | ID57 | LF1 | CGGCCAATGGCTTCAGAAA |
| | ID58 | LB1 | GGAATTGCCGGCAGAACGTC |
| SET 11 | ID59 | FIP | GGCCATTTTTTTCAGGCGGCCTTGGCGATATTTCGGTGGTC |
| | ID60 | BIP | CAAGTGATGGTGCGTTTGGTGCAGCGGCATACGCACACTA |
| | ID61 | F3 | ACGTGGTACGGTTTCTGTG |
| | ID62 | B3 | CCACCGCATCCAACACAC |
| SET 12 | ID63 | FIP | CAACACACGCTCACCGGCTGGGCGAATGTGTCGGTGATT |
| | ID64 | BIP | GCGGTAGGTGGTTCAACGGCACTACATTGCCACGTGTCAG |
| | ID65 | F3 | GGTGCGTTTGGTGCAGAA |
| | ID66 | B3 | TTCCAAGGCAACAGTTCGT |
| | ID67 | LF1 | CGTGCTGGGAATAGTGTGCGT |
| | ID68 & LB2 | LB1 | ATGTGCAGGATACGAATGTGC |
| | ID69 | LF2 | GGSAATAGTGTGCGTATGCCG |

Degenerate bases key(Y = C/T) (S = G/C)

ctrA LAMP Optimisation

The optimal operating temperature for each designed ctrA LAMP & LOOP set (60 to 65° C. inclusive) was determined by testing against N. meningitidis serogroup A strain NCTC 10025 (NmA NCTC10025) & N. meningitidis serogroup B clinical isolate 57/07 (NmB 57/07) QIAGEN total DNA extract ten fold dilutions (NB. LAMP sets 2, 8, 9 & 11 excluded due to inability to design corresponding Loop primers additionally LAMP 4 was not assessed). See Table 2 for ranking.

LAMP&LOOP primer sets were ranked based upon the following criteria;
i] Visual Sensitivity—presence of visible colour change and turbidity indicating positive reaction ie. The lowest Cut off point for NmB 57/07 & NmA NCTC10025 detectable by eye.
ii]. Speed of LAMP detection by Real Time analysis carried out on Applied Biosystems Real Time PCR instrument ABI7000 (ie Quickest ctrA LAMP for initial detection and time to reach fluorescent plateau/maximum—occurs ~10 mins after first fluorescent signal is generated see FIG. 1) iii]. ABI7000 Sensitivity (ie lowest cut off point as determined by Real Time LAMP)

Specificity

Total nucleic acid extractions from a total of 70 bacterial clinical and reference strains from 39 different bacterial species and 1 fungal reference strain were used in the present study to determine LAMP assay specificity. All designed ctrA

TABLE 2

N. meningitidis ctrA LAMP & LOOP primer set ranking (best performing No. 1 etc) with optimal operating temperature, cut off point (ctrA copies detected per reaction) & time taken in minutes to reach maximum fluorescence/Turbidity for NmA NCTC10025 & NmB 57/07 dilutions.

| RANK | LAMP & LOOP SET | OPTIMAL TEMP. | ctrA COPY NO. CUT OFF PER 25 µl REACTION | | TIME (MINS) TO REACH MAX. FLUORO. | |
|---|---|---|---|---|---|---|
| | | | NmA | NmB | NmA | NmB |
| 1 | L3L1 | 63° C. | 96.6 | 118 | 50 mins | 40 mins |
| 2 | L3L3 | 61° C. | 96.6 | 118 | 50 mins | 49 mins |
| 3 | L5L1 | 60° C.-61° C. | 96.6 | 118 | 53 mins | 60 mins |
| 4 | L13L1 | 61° C. | $1.1 \times 10^3$ | $1.1 \times 10^3$ | 47 mins | 41 mins |
| 5 | L5L3 | 62° C. | 96.6 | $1.1 \times 10^3$ | 40 mins | 49 mins |
| 6 | L12L2 | 64° C. | $1.3 \times 10^3$ | $1.1 \times 10^3$ | 60 mins | 60 mins |
| 7 | L1L1 | 63° C. | $1.6 \times 10^4$ | $1.1 \times 10^3$ | 55 mins | 57 mins |
| 8 | L12L1 | 62° C. | $1.6 \times 10^4$ | $1.6 \times 10^4$ | 51 mins | 51 mins |
| 9 | L7L6 | 60° C. | $1.6 \times 10^4$ | $1.6 \times 10^4$ | 52 mins | 50 mins |
| 10 | L7L1 | 61° C. | $1.6 \times 10^4$ | $1.6 \times 10^4$ | 60 mins | 57 mins |
| 11 | L7L2 | 60° C. | $1.3 \times 10^3$ | $1.6 \times 10^4$ | 60 mins | 55 mins |
| 12 | L6 (no loop) | 65° C. | $2.1 \times 10^5$ | $1.7 \times 10^5$ | 60 mins | 60 mins |

Final Reaction volume = 25 µl (Specimen addition = 2.5 µl/LAMP Mastermix Vol. = 22.5 µl)

Based upon sensitivity ctrA LAMP3LOOP1 (L3L1), LAMP3LOOP3 (L3L1) & LAMP5LOOP1 (L5L1) had same cut off points. Repeat investigations with L3L1, L3L3 & L5L1 confirmed findings above.

The three best performing ctrA sets L3L1, L3L3 & L5L1 were chosen for further evaluation using N. meningitidis 57/07 spiked blood specimens. Investigations were carried out to determine if increasing overall specimen addition volume from 2.5 µl to 5 µl, 10 µl and 12 µl and incorporation of a prior preheat denaturation stage of 95° C. for 5 mins for specimens followed by immediate cooling on ice would improve overall sensitivity (protocol for prior heat denaturation published by Kamachi, et al, 2006 with impressive results). Results indicated that L3L1 preheat 95° C./5 mins in combination with a 5 µl specimen addition provided greatest sensitivity and reaction speed capable of detecting 28 ctrA gene copies per reaction in less than 40 minutes. See Table 3. L3L1 with prior specimen heat denaturation plus 5 µl specimen addition was chosen for clinical validation.

LAMP & LOOP primers specifically amplified DNA from all N. meningitidis NCTC type strains and from 10 clinical isolates of N. meningitidis serogroup B. There was no cross reactivity with other Neisseria species (n=6) tested or with 54 different bacterial & fungal targets outlined in Table 4. ctrA LAMP & LOOP primers were 100% specific for capsular N. meningitidis strains tested. See FIG. 1 for example of specificity.

LAMP SETS 1, 2, 4, 7, 10 exhibited specificity for all NMG serotypes tested (A, B, C, Y, W135). SETS 8, 9, 11 will not detect NmA being specific for B, C, Y, W135 only. SETs 3, 5, 6, 10 detect all serotypes tested with wobble. SET 3 is non-A specific with C in wobble position or A specific with T in wobble position. Set 5 is non-A specific with C in wobble position, A specific and 29E with T in wobble position. Set 12 exhibits specificity for types B, C, Y, W135 with either loop primer set but detects A only using LB1/LF2 loop primers.

TABLE 3

Effect of varying specimen addition volume and heat denaturation 95° C./5 mins of NmB 57/07 spiked blood specimens on analytical sensitivity of L3L1, L3L3 & L5L1 and time in minutes required to reach maximum fluorescence.

| | Specimen Addition Volume | | | | | | | |
|---|---|---|---|---|---|---|---|---|
| | 2.5 µl | | 5 µl | | 10 µl | | 12 µl | |
| | Preheat 95° C./5 mins | No Heat | Preheat 95° C./5 mins | No Heat | Preheat 95° C./5 mins | No Heat | Preheat 95° C./5 mins | No Heat |
| L3L1 | 175 ctrA copies (32 mins) | $1.7 \times 10^3$ ctrA copies (38 mins) | 28 ctrA copies (38 mins) | 350 ctrA copies (47 mins) | 700 ctrA copies (50 mins) | $6.8 \times 10^3$ ctrA copies (44 mins) | $8.2 \times 10^3$ ctrA copies (30 mins) | $8.2 \times 10^3$ ctrA copies (41 mins) |
| L3L3 | 175 ctrA copies (35 mins) | 175 ctrA copies (36 mins) | 28 ctrA copies (45 mins) | $3.4 \times 10^3$ ctrA copies (52 mins) | 56 ctrA copies (34 mins) | 700 ctrA copies (52 mins) | 67 ctrA copies (34 mins) | 67 ctrA copies (49 mins) |
| L5L1 | 175 ctrA copies (35 mins) | $1.7 \times 10^3$ ctrA copies (45 mins) | 350 ctrA copies (38 mins) | $3.4 \times 10^3$ ctrA copies (47 mins) | 700 ctrA copies (51 mins) | $5.2 \times 10^4$ ctrA copies (34 mins) | $8.2 \times 10^3$ ctrA copies (35 mins) | $8.2 \times 10^3$ ctrA copies (41 mins) |

TABLE 4

List of bacterial and fungal species tested to determine specificity of LAMP & LOOP primer sets.

| SPECIES | STRAIN | SEROGROUP |
|---|---|---|
| Neisseria meningitidis | NCTC 10025 | A |
| Neisseria meningitidis | NCTC 10791 | Y |
| Neisseria meningitidis | NCTC 11203 | W135 |
| Neisseria meningitidis | NCTC 8554 | C |
| Neisseria meningitidis | NCTC 10792 | Z |
| Neisseria meningitidis | NCTC 10790 | X |
| Neisseria meningitidis | NCTC 11202 | 29E |
| Neisseria meningitidis | NCTC 10026, 531/07, 44/06, 217/06, 1386/06, 839/06, 368/05, 338/05, 57/07, 1069/07, 304/06 | B |
| Neisseria gonorrhoeae | ATCC 49226 | |
| Neisseria sicca | 920/06 | |
| Neisseria. flavescens | NCTC 3191 | |
| Neisseria lactamica | NCTC 10616 | |
| Neisseria cinerea | NCTC 10294 | |
| Neisseria polysaccharea | NCTC 1858 | |
| Haemophilus influenzae | NCTC 4560, 016/07 | B |
| Klebsiella pneumoniae | NCTC 10896, 45/07 | |
| Enterococcus faecalis | 009/07 | |
| Enterobacter aerogenes | NCTC 10006, 001/07 | |
| Enterobacter cloacae | NCTC 9394 | |
| Staphylococcus aureus | ATCC 25923, ATCC 29213, NCTC 10442, 09/07, M04/0071, HT2000/0132 | |
| Staphylococcus lugdunensis | RVH Isolate | |
| Staphylococcus capitis | RVH Isolate | |
| Staphylococcus sciuri | ATCC 29061 | |
| Streptococcus pneumoniae | NCTC 7465, NCTC 7978, RVHType 2, 59/07 | |
| Streptococcus parasanquis | 74/07 | |
| Streptococcus intermedius | 305/07 | |
| Micrococcus luteus | 290/07 | |
| Serratia marcescens | NCTC 10211, 287/07 | |
| Acinetobacter baumanii | 36/07 | |
| Moraxella catarrhalis | RVH01, RVH09 | |
| Escheria coli | NCTC 9001, ATCC 25922 | |
| Pseudomonas aeroginosa | 46/07 | |
| Stenotrophomonas maltophilia | ATCC 17666 | |
| Peptostreptococcus spp. | 6004-4 | |
| Bacteriodes fragilis | CAH 6046-4 | |
| Clostridium difficile | CAH 72 | |
| Sphingobacterium spiritivorum | ATCC 33861 | |
| Sphingobacterium thalpophilum | 1192/07 | |
| Acinetobacter zwoffii | 98/07 | |
| Klebsiella oxytoca ESBL + | 135/07 | |
| Burkholderia multivorans | BCH Isolate | |
| Proteus vulgaris | 564/07 | |
| Bordetella parapertussis | BCH Isolate | |
| Coxiella. burnetii | 9 Mile Strain | |
| Citrobacter freundii | NCTC 9750 | |
| Aeromonas hydrophilia | 659 | |
| Candida albicans | ATCC 10028 | |

Clinical Validation

A breakdown of L3L1 Clinical Validation results to date are outlined in Tables 5 & 6 below. All specimens underwent total nucleic acid extraction using commercially available manual Qiagen QIAamp® kit.

TABLE 5

Using ctrA Real Time Taqman PCR Assay (Corless et al, 2001) as Gold Standard for all Specimen Types Tested

| | | GOLD STANDARD | |
|---|---|---|---|
| | | POSITIVE | NEGATIVE |
| TEST | POSITIVE | TP = 24 | FP = 3 |
| | NEGATIVE | FN = 0 | TN = 233 |

Lamp Sensitivity Versus Taqman

Sensitivity=$tp/(tp+fn)$24/(24+3)×100=88.9%

In reality 2 LAMP False Positives are true positives. These were not identified by Gold Standard Taqman PCR but had been found to be positive by Manchester Reference Lab. PCR (MPCR). Considering this sensitivity=96%. One specimen was Taqman negative but repeatably LAMP positive. It is possible that this individual was harboring a capsular meningococcus (ie. Carrier state) or had low grade infection.

Lamp Specificity

Specificity=$tn/(fp+tn)$233/(3+233)×100=98.7%
(Again two False positives are in reality true positives taking this into consideration Specificity=100%)

TABLE 6

Specimen Type Breakdown % LAMP Positive

| SPECIMEN TYPE | NO. TESTED | NO. LAMP POSITIVES (%) |
|---|---|---|
| WHOLE BLOOD (B) | 73 | 7 (9.6%) |
| THROAT SWAB (TS) | 76 | 8 (10.5%) |
| EDTA BLOOD (EDTA) | 53 | 3 (5.7%) |
| SWABS (SW) | 13 | 2 (15.4%) |
| CEREBROSPINAL FLUID (CSF) | 9 | 0 (0%) |
| SERA (S) | 19 | 4 (21.1%) |
| FAECES SOLID (FS) | 2 | 1 (50%) |
| FAECES (F) | 1 | 0 (0%) |
| FAECES SEMI SOLID (FSS) | 1 | 0 (0%) |
| NASAL SECRETIONS (NASE) | 6 | 0 (0%) |
| SECRETIONS (SEC) | 3 | 1 (33.3%) |
| TRACHEA SECRETIONS (TRSE) | 1 | 1 (100%) |
| VIRAL SWAB (VIS) | 1 | 0 (0%) |
| SPUTUM | 1 | 0 (0%) |
| TOTALS | 259 | 27 (10.4%) |

Mean time (mins) to reach maximum Fluorescent intensity=28.6 mins

Range of detection=$6.6\times10^6$-$4\times10^3$ ctrA copies per ml ($3.3\times10^4$-20 ctrA copies per reaction)

Improved Accuracy of Diagnosis by LAMP on Upper Airway Secretions

Using a Likelihood Ratio analysis, based on the prevalence of true meningococcal disease in children admitted to the meningococcal care pathway in the Children's Hospital Belfast, combined with a LAMP sensitivity of 92% and specificity of 97% (allowing for a carriage rate of 2% in this age range) the Odds Ratio changes from 1:3 by clinical diagnosis to 10:1 by a LAMP diagnosis. This increased utility underlies the value of undertaking a LAMP test on upper respiratory secretions i.e. throat and nasal swabs.

Accordingly the present invention provides a series of near bedside real time LAMP assays for Neisseria meningitidis with varying specificities based on the LAMP sets and Sequence IDs set out in Table 1 and detailed in the following Sequence Listing prepared according to Patentin 3.5.

The assays of the invention can be used for early detection of *N meningitides* in samples which as easy to obtain and allow treatment of the individual to be tailored accordingly.

REFERENCES

1. Thompson M J, Ninis N, Perera R, Mayon-White R, Phillips C, Bailey L, Harnden A, Mant D, Levin M. 2006. Clinical recognition of meningococcal disease in children and adolescents. Lancet 367:397-403
2. Sadler F, Borrow R, Dawson M M, Kaczmarski E B, Cartwright K, Fox A J. 2000. Improved methods of detection of meningococcal DNA from oropharyngeal swabs from cases and contacts of meningococcal disease. Epidemiol Infect. 125:277-283
3. Dunlop K, O'Neill H, McCaughey C, Curran T, De Ornellas D, Mitchell F, Mitchell S, Feeney S, Wyatt D, Forde M, Shields M, Jackson P, Coyle P. 2005. The role of common respiratory viral infections in triggering invasive meningococcal disease. Eur Soc Clin Virology 8th Annual meeting, Geneva. Poster 38
4. Lewis C, Clarke S C. 2003. Identification of *Neisseria meningitidis* serogroups Y and W135 by siaD nucleotide sequence analysis. J Clin Microbiol. 41:2697-2699
5. Bennett D E, Cafferkey M T. 2006. Consecutive use of two multiplex PCR-based assays for simultaneous identification and determination of capsular status of nine common *Neisseria meningitidis* serogroups associated with invasive disease. J Clin Microbiol. 44:1127-1131
6. Xu J, Moore J E, Millar B C, Webb H, Shields M D, Goldsmith C E. 2005. Employment of broad range 16S rDNA PCR and sequencing in the detection of aetiological agents of meningitis. New Microbiol. 28:135-143
7. Molling P, Jacobsson S, Backman A, Olcen P. 2002. Direct and rapid identification and genogrouping of meningococci and porA amplification by LightCycler PCR. J Clin Microbiol. 40:4531-4535
8. Public Health Laboratory Service Meningococcus Forum. 2002. Guidelines for public health management of meningococcal disease in the UK. Communicable Disease and Public Health Report 5:187-204
9. Notomi, T, Okayama H, Masubuchi H, Yonekawa T, Watanabe K, Nobuyuki A, Hase T. 2000. Loop-mediated isothermal amplification of DNA. Nucleic Acids Res. 28:e63
10. Nagamine K, Watanabe K, Ohtsuka K, Hase T, Notomi T. 2001. Loop-mediated isothermal amplification using a nondenatured template. Clin Chem. 47:1742-1743
11. Nagamine K, Hase T, Notomi T. 2002. Accelerated reaction by loop-mediated isothermal amplification using loop primers. Mol Cell Probes 16:223-229
12. Soliman H & El-Metbouli, M. An inexpensive and rapid diagnostic method for Koi Herpesvirus (KHV) infection by loop-mediated isothermal amplification. 2005. Virology Journal 2:83-87
13. Mori Y, Hirano T, Notomi T. 2006. Sequence specific visual detection of LAMP reactions by addition of cationic polymers. BMC Biotechnology 6:3-7
14. Okafuji T, Yoshida N, Fujino M, Motegi Y, Ihara T, Ota Y, Notomi T, Nakayama T. 2005. Rapid Diagnostic Method for Detection of Mumps Virus Genome by Loop-Mediated Isothermal Amplification. J Clin Microbiol. 43:1625-1631
15. Yoshikawa T, Ihira M, Akimoto S, Usui C, Miyake F, Suga S, Enomoto Y, Suzuki R, Nishiyama Y, Asano Y. 2004. Detection of Human Herpesvirus 7 DNA by Loop-Mediated Isothermal Amplification. J Clin Microbiol. 42: 1348-1352
16. Seki M, Yamashita Y, Torigoe H, Tsuda H, Sato S, Maeno M. 2005. Loop-Mediated Isothermal Amplification Method Targeting the lytA Gene for Detection of *Streptococcus pneumoniae*. J Clin Microbiol. 43:1581-1586
17. Iwasaki M, Yonekawa T, Otsuka K, Suzuki W, Nagamine K, Hase T, Tatsumi K I, Horigome T, Notomi T, Kanda H. 2003. Validation of the Loop-Mediated Isothermal Amplification Method for Single Nucleotide Polymorphism Genotyping with Whole Blood. Genome Letters 2:119-126
18. Parida M, Horioke K, Ishida H, Dash P K, Saxena P, Jana A M, Islam M A, Inoue S, Hosaka N, Morita K. 2005. Rapid Detection and Differentiation of Dengue Virus Serotypes by a Real-Time Reverse Transcription-Loop-Mediated Isothermal Amplification Assay. J Clin Microbiol 43:2895-2903
19. Bossuyt P M, Reitsma J B, Bruns D E, Gatsonis C A, Glasziou P P, Irwig L M, Lijmer J G, Moher D, Rennie D, de Vet HCW (for the STARD Group). 2003. Towards Complete and Accurate Reporting of Studies of Diagnostic Accuracy: The STARD Initiative. Clin Chem. 49:1-6
20. Moher D, Schulz K F, Altman D G (for the CONSORT Group) 2001. The CONSORT statement: revised recommendations for improving the quality of reports of parallel-group randomised trials. Lancet 357:1191-1194
21. Corless, C. E., Guiver, M., Borrow, R., Edwards-Jones, V., Fox, A. J. & Kaczmarski, E. B. (2001). Simultaneous Detection of *Neisseria meningitidis, Haemophilus influenzae* and *Streptococcus pneumoniae* in suspected Cases of Meningitis and Septicemia Using Real Time PCR. Journal of Clinical Microbiology 39:1553-1558.
22. Kamachi, K., Toyoizumi-Ajisaka, H., Toda, K., Soeung, S. C., Sarath, S., Nareth, Y., Horiuchi, Y., Kojima, K., Takahashi, M. & Arakawa, Y. (2006). Development and Evaluation of a Loop Mediated Isothermal Amplification Method for Rapid Diagnosis of *Bordetella pertussis* Infection. Journal of Clinical Microbiology 44:1899-1902.
23. Tomita, N., Mori, Y., Kanda, H. & Notomi, T. (2008). Loop-mediated isothermal amplification (LAMP) of gene sequences and simple visual detection of products. Nature Protocols 3:877-882.

The invention claimed is:

1. A method of detecting meningococcal disease comprising:

amplifying by isothermal amplification at least a portion of the ctrA gene of *Neisseria meningitidis* using one or both loop-mediated isothermal amplification (LAMP) primer sets selected from the group consisting of (a) and (b) as follows:

(a) the nucleotide sequences of LAMP SET 3 L3L3, SEQ ID NOS: 11 to 14, 16 and 17; and (b) the nucleotide sequences of LAMP SET 3 L3L1, SEQ ID NOS: 11 to 16;

then detecting the amplified product.

2. The method of claim 1, wherein the primer set is LAMP SET 3 L3L3 consisting of SEQ ID NOS: 11 to 14, 16 and 17.

* * * * *